(12) United States Patent
Shimizu et al.

(10) Patent No.: US 6,586,004 B2
(45) Date of Patent: Jul. 1, 2003

(54) SOLID PREPARATION

(75) Inventors: Toshihiro Shimizu, Itami (JP); Masae Sugaya, Ikeda (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/800,748

(22) Filed: Mar. 7, 2001

(65) Prior Publication Data

US 2001/0009678 A1 Jul. 26, 2001

Related U.S. Application Data

(63) Continuation of application No. 09/424,434, filed as application No. PCT/JP98/02298 on May 26, 1998, now Pat. No. 6,299,904.

(30) Foreign Application Priority Data

May 27, 1997 (JP) .............................. 9-136724

(51) Int. Cl.⁷ .............................. A61K 9/20; A61K 9/14; A61K 47/38
(52) U.S. Cl. .................. 424/464; 424/465; 514/781
(58) Field of Search .................. 424/464, 435, 424/494, 488, 465, 479, 468, 489, 480; 514/781

(56) References Cited

U.S. PATENT DOCUMENTS

| | | | |
|---|---|---|---|
| 5,501,861 A | * 3/1996 | Makino et al. | 424/464 |
| 5,855,914 A | * 1/1999 | Koyama et al. | 424/494 |
| 5,958,453 A | 9/1999 | Ohno et al. | 424/465 |
| 6,248,357 B1 | 6/2001 | Ohno et al. | 424/465 |

FOREIGN PATENT DOCUMENTS

| | | | |
|---|---|---|---|
| EP | 0553777 A2 A3 | | 8/1993 |
| EP | 0745382 | | 12/1996 |
| EP | 0839526 A | | 5/1998 |
| EP | 0 922464 A1 | | 6/1999 |
| JP | 54-11226 | | 1/1979 |
| JP | 4-66538 | | 3/1992 |
| JP | 05310558 | * | 11/1993 |
| JP | 6-100601 | | 4/1994 |
| JP | 06 305962 | | 11/1994 |
| JP | 07 017853 | | 1/1995 |
| JP | 8-310969 | | 11/1996 |
| JP | 09 048726 | | 2/1997 |
| JP | 9-71523 | | 3/1997 |
| JP | 09 071523 | | 3/1997 |

* cited by examiner

*Primary Examiner*—James M. Spear
*Assistant Examiner*—Blessing M. Fubara
(74) *Attorney, Agent, or Firm*—Mark Chao; Elaine M. Ramesh

(57) ABSTRACT

A solid preparation which comprises (i) a pharmaceutically active ingredient, (ii) one or more water-soluble sugar alcohol selected from the group consisting of sorbitol, maltitol, reduced starch saccharide, xylitol, reduced palatinose and erythritol, and (iii) low-substituted hydroxypropylcellulose having hydroxypropoxyl group contents of 7.0 to 9.9 percent by weight; which exhibits excellent buccal disintegration and dissolution and also appropriate strength.

19 Claims, No Drawings

SOLID PREPARATION

This application is a continuation of U.S. patent application Ser. No. 09/424,434 filed Nov. 23, 1999, now U.S. Pat. No. 6,299,904, issued Oct. 9, 2001, which was the National Phase filing of International Patent Application Serial No. PCT/JP98/02298, filed May 26, 1998.

TECHNICAL FIELD

The present invention relates to a solid preparation, especially a preparation capable of buccal disintegration or dissolution, having characteristics of fast disintegration or dissolution in the oral cavity even without water.

BACKGROUND ART

There has been a demand for development of a pharmaceutical preparation capable of buccal disintegration or dissolution, which can be, if necessary, administered readily even without water, by aged people and children anywhere or anytime. Examples of prior art references disclosing such preparation are shown below.

JP-A H9(1997)-48726 discloses rapid buccal dissolution type preparations comprising a drug and a material wetting in a mouldable way on humidifying and retaining a shape after moulding and drying. Such material is exemplified by sugars, sugar alcohols, and water-soluble polymers.

JP-A H5(1993)-271054 (EP-A 553777) discloses a method of producing a rapid buccal dissolution type tablets comprising a pharmacologically active ingredient and sugars.

JP-A H9(1997)-71523 discloses tablets with rapid disintegration in the oral cavity which comprise a drug, crystalline cellulose, low-substituted hydroxypropylcellulose and a lubricant.

However, these prior art references nowhere disclose a solid preparation comprising (1) a pharmaceutically active ingredient, (2) one or more water-soluble sugar alcohols selected from the group consisting of sorbitol, maltitol, reduced starch saccharide, xylitol, reduced palatinose and erythritol, and (3) low-substituted hydroxypropylcellulose having hydroxypropoxyl group contents of 7.0 to 9.9 percent by weight.

There has been a demand for development of a solid preparation which exhibits excellent buccal disintegration and dissolution and also an appropriate strength (hardness) such that the solid preparation never disintegrates or suffers damage in the course of the production steps or distribution stages.

DISCLOSURE OF INVENTION

The present invention relates to a solid preparation comprising (1) a pharmaceutically active ingredient, (2) one or more water-soluble sugar alcohol selected from the group consisting of sorbitol, maltitol, reduced starch saccharide, xylitol, reduced paratinose and erythritol (hereafter also referred to as a water-soluble sugar alcohol), and (3) low-substituted hydroxypropylcellulose having hydroxypropoxyl group contents of 7.0 to 9.9 percent by weight.

The present invention further relates to use of low-substituted hydroxypropylcellulose having hydroxypropoxyl group contents of 7.0 to 9.9 percent by weight for the manufacture of a pharmaceutical preparation capable of buccal disintegration or dissolution.

The present invention further relates to method of improving buccal disintegration or dissolution of a solid pharmaceutical preparation characterized by using low-substituted hydroxypropylcellulose having hydroxypropoxyl group contents of 7.0 to 9.9 percent by weight.

The pharmaceutically active ingredient to be used in the present invention may be in any optional form, for example, a solid, powder or granular, crystalline, oily or solution form.

As the pharmaceutically active ingredient, for instance, there may be mentioned one or more ingredients selected from the group consisting of nourishing and health-promoting agents, antipyretic-analgesic-antiinflammatory agents, antipsychotic drugs, antianxiety drugs, antidepressants, hypnotic-sedatives, spasmolytics, central nervous system affecting drugs, cerebral metabolism ameliolators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, antidiabetic agents, drugs for osteoporosis, skeletal muscle relaxants, antidinics, hormones, alkaloid narcotics, sulfa drugs, antipodagrics, anticoagulants, anti-malignant tumor agents, agents for alzheimer's disease, etc.

Examples of the nourishing and health-promoting agents include vitamins such as vitamin A, vitamin D, vitamin E (d-α-tocopherol acetate, etc.), vitamin $B_1$ (dibenzoylthiamine, fursultiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), vitamin $B_{12}$ (hydroxocobalamin acetate, etc.), etc.; minerals such as calcium, magnesium and iron; proteins, amino acids, oligosaccharides, crude drugs, etc.

Examples of the antipyretic-analgesic-antiinflammatory agents include aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serratiopeptidase, lysozyme chloride, tolfenamic acid, mefenamic acid, diclofenac sodium, flufenamic acid, salicylamide, aminopyrine, ketoprofen, indomethacin, bucolome, pentazocine, etc.

Examples of the antipsychotic drugs include chlorpromazine, reserpine, etc.

Examples of the antianxiety drugs include alprazolam, chlordiazepoxide, diazepam, etc.

Examples of the antidepressants include imipramine, maprotiline, amphetamine, etc.

Examples of the hypnotic-sedatives include estazolam, nitrazepam, diazepam, perlapine, phenobarbital sodium, etc.

Examples of the spasmolytics include scopolamine hydrobromide, diphenhydramine hydrochloride, papaverine hydrochloride, etc.

Examples of the central nervous system affecting drugs include citicoline, rotirenine, etc.

Examples of the cerebral metabolism ameliolators include vinpocetine, meclofenoxate hydrochloride, etc.

Examples of the antiepileptics include phenytoin, carbamazepine, etc.

Examples of the sympathomimetic agents include isoproterenol hydrochloride, etc.

Examples of the gastrointestinal function conditioning agents include stomachic-digestives such as diastase, saccharated pepsin, scopolia extract, cellulase AP3, lipase AP, cinnamon oil, etc.; intestinal function controlling drugs such as perperine hydrochloride, resistant lactic acid bacterium, *Lactobacillus bifidus*, etc.

Examples of the antacids include magnesium carbonate, sodium hydrogen carbonate, magnesium aluminometasilicate, synthetic hydrotalcite, precipitated calcium carbonate, magnesium oxide, etc.

Examples of the antiulcer agents include lansoprazole, omeprazole, rabeprazole, pantoprazole, famotidine, cimetidine, ranitidine hydrochloride, etc.

Examples of the antitussive-expectorants include chloperastine hydrochloride, dextromethorphan hydrobromide, theophylline, potassium guaiacolsulfonate, guaifenesin, codeine phosphate, etc.

Examples of the antiemetics include diphenidol hydrochloride, metoclopramide, etc.

Examples of the respiratory stimulants include levallorphan tatrate, etc.

Examples of the bronchodilators include theophylline, salbutamol sulfate, etc.

Examples of the antiallergic agents include amlexanox, seratrodast, etc.

Examples of the dental buccal drugs include oxytetracycline, triamcinolone acetonide, chlorhexidine hydrochloride, lidocaine, etc.

Examples of the antihistamines include diphenhydramine hydrochloride, promethazine, isothipendyl hydrochloride, dl-chlorpheniramine maleate, etc.

Examples of the cardiotonics include caffeine, digoxin, etc.

Examples of the antiarryhythmic agents include procainamide hydrochloride, propranolol hydrochloride, pindolol, etc.

Examples of the diuretics include isosorbide, furosemide, etc.

Examples of the hypotensive agents include delapril hydrochloride, captopril, hexamethonium bromide, hydralazine hydrochloride, labetalol hydrochloride, manidipine hydrochloride, candesartan cilexetil, methyldopa, losartan, valsartan, eprosartan, irbesartan, tasosartan, telmisartan, pomisartan, ripisartan, forasartan, etc.

Examples of the vasoconstrictors include phenylephrine hydrochloride, etc.

Examples of the coronary vasodilators include carbocromen hydrochloride, molsidomine, verapamil hydrochloride, etc.

Examples of the peripheral vasodilators include cinnarizine, etc.

Examples of the antihyperlipidemic agents include cerivastatin sodium, simvastatin, pravastatin sodium, etc.

Examples of the cholagogues include dehydrocholic acid, trepibutone, etc.

Examples of the antibiotics include cephem antibiotics such as cefalexin, amoxicillin, pivmecillinam hydrochloride, cefotiam dihydrochloride, cefozopran hydrochloride, cefmenoxime hydrochloride, cefsluodin sodium, etc.; synthetic antibacterials such as ampicillin, cyclacillin, sulbenicillin sodium, nalidixic acid, enoxacin, etc.; monobactam antibiotics such as carumonam sodium; penem antibiotics, carbapenem antibiotics, etc.

Examples of the chemotherapeutic agents include sulfamethizole hydrochloride, thiazosulfone, etc.

Examples of the antidiabetic agents include tolbutamide, voglibose, pioglitazone (hydrochloride), troglitazone, 5-[[4-[2-(methyl-2-pyridinylamino)ethoxy]phenyl]methyl]-2,4-thiazolidinedione (BRL-49653), acarbose, miglitol, emiglitate, etc.

Examples of the drugs for osteoporosis include ipriflavone, etc.

Examples of the skeletal muscle relaxants include methocarbamol, etc.

Examples of the antidinics include meclizine hydrochloride, dimenhydrinate, etc.

Examples of the hormones include riothyroinine sodium, dexamethasone sodium phosphate, prednisolone, oxendolone, leupororelin acetate, etc.

Examples of the alkaloid narcotics include opium, morphine hydrochloride, ipecac, oxycodone hydrochloride, opium alkaloids hydrochlorides, cocaine hydrochloride, etc.

Examples of the sulfa drugs include sulfanilamide, sufamethizole, etc.

Examples of the antipodagrics include allopurinol, colchicine, etc.

Examples of the anticoagulants include dicoumarol, etc.

Examples of the anti-malignant tumor agents include 5-fluorouracil, uracil, mitomycin, etc.

Examples of the agents for alzheimer's disease include idebenone, vinpocetine, etc.

The pharmaceutically active ingredients may be coated, by the per se known method, for masking the taste and odor or for enteric dissolution or sustained release. The coating material that can be employed includes, for instance, enteric coating polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose, etc.; gastric coating polymers such as polyvinylacetal diethylaminoacetate, aminoalkyl methacrylate copolymer, etc.; water-soluble polymers such as hydroxypropylcellulose, hydroxypropylmethylcellulose, etc.; water-insoluble polymers such as ethylcellulose, aminoalkyl methacrylate copolymer RS, ethylacrylate methylmethacrylate copolymer, etc.; wax, etc.

The above pharmaceutically active ingredients are used, for instance, in an amount of 0.01 to 70 weight parts, preferably 0.02 to 50 weight parts, more preferably 0.05 to 30 weight parts, per 100 weight parts of a solid preparation.

Among the above pharmaceutically active ingredients, nourishing and health-promoting agents, antipyretic-analgesic-antiinflammatory agents, hypnotic-sedatives, central nervous system affecting drugs, gastrointestinal function conditioning agents, antiulcer agents, antitussive-expectorants, antiallergic agents, antiarrhythmic agents, diuretics, hypotensive agents, vasoconstrictors, coronary vasodilators, antihyperlipidemic agents, antidiabetic agents, drugs for osteoporosis, skeletal muscle relaxants and antidinics are preferably employed.

The pharmaceutically active ingredients especially preferably employed in the present invention are lansoprazole, voglibose and candesartan cilexetil.

In the present invention, a water-soluble sugar alcohol means a water-soluble sugar alcohol which needs water in an amount of less than 30 ml when 1 g of a water-soluble sugar alcohol is added to water and dissolved within about 30 minutes at 20° C. by strongly shaking every 5 minutes for 30 seconds.

As the water-soluble sugar alcohol, sorbitol, maltitol, reduced starch saccharide, xylitol, reduced palatinose or erythritol is employed. Two or more of these water-soluble sugar alcohols can be used as a mixture in a given ratio.

The water-soluble sugar alcohol is preferably xylitol or erythritol, especially preferably erythritol. As erythritol, one that is produced by fermentation with yeasts using glucose as the starting material, and that has a particle size of at most 50 mesh is used. Such erythritol is available as a product on the market such as a product manufactured by Nikken Chemical Co., Ltd. (Japan), etc.

The water-soluble sugar alcohol is used, for instance, in an amount of 5 to 97 weight parts, preferably 10 to 90 weight parts, per 100 weight parts of a solid preparation. If the amount of the water-soluble sugar alcohol to be used is too much compared with such ranges, sufficient strength of a preparation can not be obtained. On the contrary, the amount of the water-soluble sugar alcohol to be used is too small, sufficient buccal disintegration or dissolution can not be obtained. Both of these are not preferable.

The hydroxypropoxyl group contents of a low-substituted hydroxypropylcellulose employed in the present invention range from 7.0 to 9.9 percent by weight.

Examples of the low-substituted hydroxypropylcellulose having hydroxypropoxyl group contents of 7.0 to 9.9 percent by weight include LH-22, LH-32, and mixtures thereof. These are available as a product on the market such as a product manufactured by Shin-Etsu Chemical Co., Ltd. (Japan).

The low-substituted hydroxypropylcellulose having hydroxypropoxyl group contents of 7.0 to 9.9 percent by weight is used in an amount of 3 to 50 weight parts, preferably 5 to 40 weight parts, per 100 weight parts of a solid preparation. If the amount of the low-substituted hydroxypropylcellulose to be used is too much compared with such ranges, sufficient buccal disintegration or dissolution can not be obtained. On the contrary, the amount of the low-substituted hydroxypropylcellulose to be used is too small, sufficient strength of a preparation can not be obtained. Both of these are not preferable.

Thus, buccal disintegration or dissolution in a solid preparation can be improved by using low-substituted hydroxypropylcellulose having hydroxypropoxyl group contents of 7.0 to 9.9 percent by weight.

The solid preparation of the present invention is useful especially as a preparation which is capable of buccal disintegration or dissolution, and administered without water or together with water.

The dosage forms of a solid preparation of the present invention includes tablets, granules, fine granules, etc., with preference given to tablets.

Unless buccal disintegration or dissolution, or strength of a preparation is interfered with, a solid preparation of the present invention may further contain a variety of additives which are commonly employed in the manufacture of preparations in general dosage forms. The amount of such additives to be used is one commonly employed in the manufacture of preparations in general dosage forms.

Such additives include, for instance, binders, acids, foaming agents, artificial sweeteners, flavorants, lubricants, colorants, stabilizers, disintegrators, etc.

Examples of the binders include hydroxypropylcellulose, hydroxypropylmethylcellulose, crystalline cellulose, pregelatinized starch, polyvinylpyrrolidone, gum arabic powder, gelatin, pullulan, etc. The use of crystalline cellulose as the binders provides a solid preparation which exhibits more excellent strength of a preparation while retaining excellent buccal disintegration and dissolution. Such crystalline cellulose includes one that is called microcrystalline cellulose. Examples of the crystalline cellulose include CEOLUS KG801, avicel PH101, avicel PH102, avicel PH301, avicel PH302, avicel RC-A591NF (crystalline cellulose carmellose sodium), etc. Among these, preferably employed is CEOLUS KG801 which is also called crystalline cellulose of high compressibility. Two or more of the crystalline cellulose can be used as a mixture in a given ratio. Such crystalline cellulose is available as a product on the market such as a product manufactured by Asahi Chemical Co., Ltd. (Japan). Crystalline cellulose is used, for instance, in an amount of about 3 to 50 weight parts, preferably about 5 to 40 weight parts, more preferably about 5 to 20 weight parts, per 100 weight parts of a solid preparation.

Examples of the acids include citric acid, tartaric acid, malic acid, etc.

Examples of the foaming agents include sodium hydrogen carbonate, etc.

Examples of the artificial sweeteners include saccharin sodium, dipotassium glycyrrhizinate, aspartame, stevia, thaumatin, etc.

Examples of the flavorants include lemon, lemon lime, orange, menthol, etc.

Examples of the lubricants include magnesium stearate, sucrose fatty acid ester, polyethyleneglycol, talc, stearic acid, etc. The use of polyethyleneglycol as the lubricants provides a stable solid preparation in which decomposition of a pharmaceutically active ingredient with the lapse of day is suppressed. In this case, polyethyleneglycol is used, for instance, in an amount of 0.01 to 10 weight parts, preferably 0.1 to 5 weight parts, per 100 weight parts of a solid preparation.

Examples of the colorants include various food colorants (e.g. Food Yellow No. 5, Food RED No. 2, Food Blue No. 2, etc.), food lakes, red iron oxide, etc.

Examples of the stabilizers include a basic substance in the case of a basic pharmaceutically active ingredient, and an acidic substance in the case of an acidic pharmaceutically active ingredient.

Examples of the disintegrators include those called super disintegrators and exemplified by crospovidone [manufactured by ISP Inc. (U.S.A.), BASF (Germany)], croscarmellose sodium [FMC-Asahi Chemical Co., Ltd. (Japan)], carmellose calcium [Gotoku Chemical (Yakuhin), (Japan)]; hydroxypropylcellulose; carboxymethylstarch sodium [Matsutani Chemical Co., Ltd. (Japan)]; corn starch, etc., with preference given to crospovidone. Two or more of these disintegrators can be used as a mixture in a given ratio.

As crospovidone, any cross-linked homopolymer called 1-ethenyl-2-pyrrolidinone homopolymer may be used, and usually crospovidone having a molecular weight of at least 1,000,000 is used. Specific examples of crospovidone available as a product on the market include Cross-linked povidone, Kollidon CL [manufactured by BASF (Germany)], Polyplasdone XL, Polyplasdone XL-10, INF-10 [manufactured by ISP Inc. (U.S.A.)], polyvinylpolypyrrolidone, PVPP and 1-vinyl-2-pyrrolidinone homopolymer.

The disintegrator is used, for instance, in an amount of 0.1 to 20 weight parts, preferably 1 to 10 weight parts, per 100 weight parts of a solid preparation.

When a pharmaceutically active ingredient is one that is unstable to an acid, such as lansoprazole, omeprazole, rabeprazole, pantoprazole, etc., an basic inorganic salt is preferably incorporated for the purpose of stabilizing the pharmaceutically active ingredient in a solid preparation. Examples of the basic inorganic salt include basic inorganic salts of sodium, potassium, magnesium and/or calcium. Two or more of these basic inorganic salts can be used as a mixture in a given ratio.

Examples of the basic inorganic salts of sodium include sodium carbonate, sodium hydrogen carbonate, etc.

Examples of the basic inorganic salts of potassium include potassium carbonate, potassium hydrogen carbonate, sodium potassium carbonate, etc.

Examples of the basic inorganic salts of magnesium include heavy magnesium carbonate, magnesium carbonate, magnesium oxide, magnesium hydroxide, magnesium metasilicate aluminate, magnesium silicate aluminate, magnesium silicate, magnesium aluminate, synthetic hydrotalcite [$Mg_6Al_2(OH)_{16}.CO_3.4H_2O$] and aluminum magnesium hydroxide [$2.5MgO.Al_2O_3.xH_2O$], with preference given to heavy magnesium carbonate, magnesium carbonate, magnesium oxide, magnesium hydroxide, etc.

Examples of the basic inorganic salts of calcium include precipitated calcium carbonate, calcium hydroxide, etc.

The basic inorganic salt is preferably, a basic inorganic salt of magnesium, more preferably heavy magnesium carbonate, magnesium carbonate, magnesium oxide, magnesium hydroxide.

The amount of the basic inorganic salt to be used is appropriately selected depending on kinds of the basic inorganic salt and is, for instance, about 0.3 to 200 percents by weight, preferably about 1 to 100 percents by weight, more preferably about 10 to 50 percents by weight, especially preferably about 20 to 40 percents by weight, based on a pharmaceutically active ingredient.

The solid preparation of the present invention can be produced in accordance with a conventional method in the fields of pharmaceutics. Such methods include, for instance, a method which comprises blending, if necessary after addition of water, a pharmaceutically active ingredient, a water-soluble sugar alcohol and low-substituted hydroxypropylcellulose having hydroxypropoxyl group contents of 7.0 to 9.9 percent by weight, and molding, if necessary followed by drying. Here, the solid preparation of the present invention can be produced without using water.

The blending procedure can be carried out by any of the conventional blending techniques such as admixing, kneading, granulating, etc. The blending procedure is carried out, for instance, by using an apparatus such as Vertical Granulator GV10 [manufactured by Powrex Corp. (U.S.A.)], Universal Kneader [manufactured by Hata Iron Works Co., Ltd. (Japan)] and fluidized bed granulator LAB-1 and FD-3S [manufactured by Powrex Corp. (U.S.A.)].

The molding procedure can be carried out, for instance, by tabletting with a pressure of 0.5 to 3 ton/cm$^2$ by using a single-punch tabletting machine [Kikusui Seisakusho (Japan)] or a rotary type tabletting machine [Kikusui Seisakusho (Japan)] when a solid preparation is a tablet.

The drying procedure can be carried out by any of the techniques used commonly in the art, such as vacuum drying, fluidized-bed drying, etc.

The solid preparation of the present invention thus obtained exhibits fast disintegrability or dissolubility in the buccal cavity, and also an appropriate strength of preparation.

The buccal dissolution time of the solid preparation of the present invention (the time for healthy male or female adults to complete disintegration of a solid preparation by buccal saliva) is usually about 5 to about 50 seconds, preferably about 5 to about 40 seconds, more preferably about 5 to about 30 seconds.

The strength of the solid preparation of the present invention (measurement with a tablet hardness tester) is usually about 2 to about 20 kg, preferably about 4 to about 15 kg.

The solid preparation of the present invention can be safely administered orally to mammals such as mice, rats, rabbits, cats, dogs, bovines, horses, monkeys, humans, etc.

While the dosage varies depending on kinds of a pharmaceutically active ingredient, a subject, diseases, etc., the dosage can be selected so that the dosage of the pharmaceutically active ingredient is an effective amount.

For instance, when lansoprazole is employed as a pharmaceutically active ingredient, the solid preparation of the present invention is useful for treatment and prophylaxis of digestive ulcer (e.g., gastric ulcer, duodenal ulcer, anastomotic ulcer, Zollinger-Ellison syndrome, etc), gastritis, reflux esophagitis, etc.; eradication of *H. pyroli;* suppression of gastrointestinal bleeding caused by digestive ulcer, acute stress ulcer and hemorrhagic gastritis; suppression of gastrointestinal bleeding caused by invasive stress (e.g., stress caused by cerebrovascular disease, head injury, failure of many organs, burn injury of a wide range, which necessitate a large-scale operation necessitating the following intensive management, or intensive care); treatment and prophylaxis of ulcer caused by non-steroidal anti-inflammatory agent; treatment and prophylaxis of gastric hyperacidity and ulcer caused by postoperative stress; administration before anesthesia, etc., and the dosage thereof per an adult (body weight: 60 kg) is 0.5 to 1500 mg/day, preferably 5 to 150 mg/day, as lansoprazole.

When voglibose is employed as a pharmaceutically active ingredient, the solid preparation of the present invention is useful for treatment and prophylaxis of obesity, adiposity, hyperlipemia, diabetes, etc., and the dosage thereof per an adult (body weight: 60 kg) is 0.01 to 30 mg/day, preferably 0.1 to 3 mg/day, as voglibose. This solid preparation can be administered once a day, or two or three times separately a day.

Further, when candesartan cilexetil is employed as a pharmaceutically active ingredient, the solid preparation of the present invention is useful for treatment and prophylaxis of hypertension, cardiac diseases, cerebral apoplexy, renal diseases, etc., and the dosage thereof per an adult (body weight: 60 kg) is 1 to 50 mg/day, preferably 2 to 30 mg/day, as candesartan cilexetil.

BEST MODE FOR CARRYING OUT THE INVENTION

The following Working Examples and Comparative Examples are further illustrative but by no means limitative of the present invention.

The physical properties of the tablets prepared in Working Examples and Comparative Examples were determined by the following test methods.

(1) Hardness Test

Determination was carried out with a tablet hardness tester [manufactured by Toyama Sangyo, Co. Ltd. (Japan)]. The test was performed in 10 runs and mean values were shown.

(2) Buccal Disintegration Time

Time for complete disintegration or dissolution only by saliva in the buccal cavity was determined.

WORKING EXAMPLE 1

A fluidized bed granulator [manufactured by Powrex Corp. (U.S.A.), LAB-1] was charged with 0.8 g of voglibose, 636.8 g of erythritol [manufactured by Nikken Chemical Co., Ltd. (Japan)] and 160.0 g of low-substituted hydroxypropylcellulose LH-32 [hydroxypropoxyl group contents of 8.8% by weight, manufactured by Shin-Etsu Chemical Co., Ltd. (Japan)], and granulation was carried out while spraying distilled water. The granules were dried and then 2.4 g of magnesium stearate was added. The mixture was tabletted using a rotary type tabletting machine with a punch having a beveled edge, 10 mm in diameter, at a tabletting pressure of 1.5 ton/cm$^2$, to provide tablets each weighing 400 mg.

The hardness and buccal disintegration time of each tablet thus obtained were 6.1 kg and 27 seconds respectively.

WORKING EXAMPLE 2

A fluidized bed granulator [manufactured by Powrex Corp. (U.S.A.), LAB-1] was charged with 32.0 g of candesartan cilexetil, 862.8 g of erythritol [manufactured by Nikken Chemical Co., Ltd. (Japan)], 240.0 g of low-substituted hydroxypropylcellulose LH-32 [hydroxypropoxyl group contents of 8.8% by weight, manufactured by Shin-Etsu Chemical Co., Ltd. (Japan)], 1.6 g of polyethylene glycol [manufactured by Sanyo Kasei Kogyo Co., Ltd. (Japan)] and 60.0 g of crospovidone, and granulation was carried out while spraying distilled water. The granules were dried and then 3.6 g of magnesium stearate was added. The mixture was tabletted using a rotary type tabletting machine with a punch having a beveled edge, 10 mm in diameter, at a tabletting pressure of 1.0 ton/cm$^2$, to provide tablets each weighing 300 mg.

The hardness and buccal disintegration time of each tablet thus obtained were 6.1 kg and 21 seconds respectively.

WORKING EXAMPLE 3

A fluidized bed granulator [manufactured by Powrex Corp. (U.S.A.), FD-3SN] was charged with 32.0 g of candesartan cilexetil, 922.8 g of erythritol [manufactured by Nikken Chemical Co., Ltd. (Japan)], 240.0 g of low-substituted hydroxypropylcellulose LH-32 [hydroxypropoxyl group contents of 8.8% by weight, manufactured by Shin-Etsu Chemical Co., Ltd. (Japan)] and 1.6 g of polyethylene glycol [manufactured by Sanyo Kasei Kogyo Co., Ltd. (Japan)], and granulation was carried out while spraying distilled water. The granules were dried and then 3.6 g of magnesium stearate was added. The mixture was tabletted using a rotary type tabletting machine with a punch having a beveled edge, 10 mm in diameter, at a tabletting pressure of 1.0 ton/cm$^2$, to provide tablets each weighing 300 mg.

The hardness and buccal disintegration time of each tablet thus obtained were 7.1 kg and 22 seconds respectively.

WORKING EXAMPLE 4

A fluidized bed granulator [manufactured by Powrex Corp. (U.S.A.), FD-3SN] was charged with 32.0 g of candesartan cilexetil, 924.4 g of erythritol [manufactured by Nikken Chemical Co., Ltd. (Japan)] and 240.0 g of low-substituted hydroxypropylcellulose LH-32 [hydroxypropoxyl group contents of 8.8% by weight, manufactured by Shin-Etsu Chemical Co., Ltd. (Japan)], and granulation was carried out while spraying distilled water. The granules were dried and then 3.6 g of magnesium stearate was added. The mixture was tabletted using a rotary type tabletting machine with a punch having a beveled edge, 10 mm in diameter, at a tabletting pressure of 1.0 ton/cm$^2$, to provide tablets each weighing 300 mg.

The hardness and buccal disintegration time of each tablet thus obtained were 8.5 kg and 22 seconds respectively.

WORKING EXAMPLE 5

(1) Production of Powders Having a Core

A centrifugal fluidized coating granulator [manufactured by Powrex Corp. (U.S.A.), MP-10] was charged with 300 g of Nonpareil 105 (particle diameter of 100 to 200 µm). While the inlet air temperature and the temperature of the loading were being controlled at 85° C. and about 28° C. respectively, the Nonpareil was coated by spraying a bulk liquid of the following composition prepared in advance in accordance with the tangential spray method at a spray rate of 20 g/min. The spraying operation was stopped when the specified amount of the bulk liquid had been sprayed, and then drying was carried out in the granulator for 7 minutes. The resulting granules were sieved through a #60 circular sieve (250 µm) and #100 circular sieve (150 µm) to provide 750 g of powder having a core.

| [Bulk liquid] | |
|---|---|
| Lansoprazole | 300 g |
| Magnesium carbonate | 100 g |
| Low-substituted hydroxypropylcellulose LH-32 | 50 g |
| Hydroxypropylcellulose (Type SSL) | 100 g |
| Water | 1650 g |

(2) Production of Film-Undercoated Powders Having a Core

A centrifugal fluidized coating granulator [manufactured by Powrex Corp. (U.S.A.), MP-10] was charged with 680 g of the above powders having a core. While the inlet air temperature and the temperature of the loading were being controlled at 70° C. and about 36° C. respectively, an undercoating liquid of the following composition prepared in advance was sprayed in accordance with the tangential spray method at a spray rate of 10 g/min. to provide 650 g of film-undercoated powder having a core.

| [Undercoating liquid] | |
|---|---|
| Hydroxypropylmethylcellulose (Type 2910, viscosity of 3 centistokes) | 32 g |
| Talc | 8 g |
| Water | 760 g |

(3) Production of Enteric-Coated Powders Having a Core

A centrifugal fluidized coating granulator [manufactured by Powrex Corp. (U.S.A.), MP-10] was charged with 450 g of the above film-undercoated powders having a core. While the inlet air temperature and the temperature of the loading were being controlled at 65° C. and about 36° C. respectively, an enteric film coating liquid of the following composition prepared in advance was sprayed in accordance with the tangential spray method at a spray rate of 17 g/min. The coated powders were dried in vacuum at 40° C. for 16 hours, and sieved through a #42 circular sieve (355 µm) and a #80 circular sieve (177 µm) to provide 950 g of enteric-coated powders having a core.

| [Enteric film coating liquid] | |
|---|---|
| Eudragit L30D-55 | 1078.3 g |
| Eudragit NE30D | 138.5 g |
| Triethyl citrate | 46.0 g |
| Glyceryl monostearate | 23.1 g |
| Talc | 16.0 g |
| Polysorbate 80 | 9.0 mg |
| Yellow iron oxide | 0.5 g |
| Water | 2038.5 g |

(4) Production of Granulated Powders

A fluidized bed granulator [manufactured by Powrex Corp. (U.S.A.), LAB-1] was charged with 1321.2 g of erythritol [manufactured by Nikken Chemical Co., Ltd. (Japan)], 360.0 g of low-substituted hydroxypropylcellulose LH-32 [hydroxypropoxyl group contents of 8.8% by weight, manufactured by Shin-Etsu Chemical Co., Ltd. (Japan)], 18.0 g of anhydrous citric acid, and 1.8 g of aspartame, and granulation was carried out while spraying a solution which was prepared by dissolving 3.6 g of polyethylene glycol (PEG-6000) in 896.4 ml of distilled water. The granules were dried to provide granulated powders. To the granulated powders were added 90.0 g of crospovidone and 5.4 g of magnesium stearate, which was admixed in a bag to give mixed powders, (5) Production of Tablets Capable of Buccal Disintegration or Dissolution 200.0 g of the above enteric-coated powders having a core and 300.0 g of the above mixed powders were tabletted using an autograph with a punch having a beveled edge, 11 mm in diameter, at a tabletting pressure of 1.0 ton/cm², to provide tablets each weighing 500 mg.

The hardness and buccal disintegration time of each tablet thus obtained were 4.2 kg and 27 seconds respectively.

WORKING EXAMPLE 6

A fluidized bed granulator [manufactured by Powrex Corp. (U.S.A.), LAB-1] was charged with 0.8 g of voglibose, 895.6 g of erythritol [manufactured by Nikken Chemical Co., Ltd. (Japan)], 240.0 g of low-substituted hydroxypropylcellulose LH-32 [hydroxypropoxyl group contents of 8.8% by weight, manufactured by Shin-Etsu Chemical Co., Ltd. (Japan)] and 60.0 g of crospovidone, and granulation was carried out while spraying distilled water. The granules were dried and then 3.6 g of magnesium stearate was added. The mixture was tabletted using a rotary type tabletting machine with a punch having a beveled edge, 10 mm in diameter, at a tabletting pressure of 1.0 ton/cm², to provide tablets each weighing 300 mg.

The hardness and buccal disintegration time of each tablet thus obtained were 7.0 kg and 17 seconds respectively.

WORKING EXAMPLE 7

A fluidized bed granulator [manufactured by Powrex Corp. (U.S.A.), LAB-1] was charged with 0.8 g of voglibose, 871.6 g of erythritol [manufactured by Nikken Chemical Co., Ltd. (Japan)], 240.0 g of low-substituted hydroxypropylcellulose LH-32 [hydroxypropoxyl group contents of 8.8% by weight, manufactured by Shin-Etsu Chemical Co., Ltd. (Japan)], 24.0 g of crospovidone and 60.0 g of CEOLUS KG 801 [manufactured by Asahi Chemical Co., Ltd. (Japan)], and granulation was carried out while spraying distilled water. The granules were dried and then 3.6 g of magnesium stearate was added. The mixture was tabletted using a rotary type tabletting machine with a punch having a beveled edge, 10 mm in diameter, at a tabletting pressure of 1.0 ton/cm², to provide tablets each weighing 300 mg.

The hardness and buccal disintegration time of each tablet thus obtained were 10.4 kg and 24 seconds respectively.

Comparative Example 1

Tablets were produced in the same manner as in Working Example 1 except that low-substituted hydroxypropylcellulose LH-32 was replaced by low-substituted hydroxypropylcellulose LH-31 [hydroxypropoxyl group contents of 11.0% by weight, manufactured by Shin-Etsu Chemical Co., Ltd. (Japan)].

The hardness and buccal disintegration time of each tablet thus obtained were 8.4 kg and 77 seconds respectively.

Comparative Example 2

Tablets were produced in the same manner as in Working Example 1 except that low-substituted hydroxypropylcellulose LH-32 was replaced by low-substituted hydroxypropylcellulose LH-30 [hydroxypropoxyl group contents of 14.6% by weight, manufactured by Shin-Etsu Chemical Co., Ltd. (Japan)].

The hardness and buccal disintegration time of each tablet thus obtained were 6.8 kg and 51 seconds respectively.

INDUSTRIAL APPLICABILITY

The solid preparation of the present invention possesses excellent disintegrability or dissolubility, and is used for treatment or prophylaxis of various diseases as a preparation capable of buccal disintegration or dissolution which can be administered without water by aged people and children anywhere or anytime.

Further, the solid preparation also possesses an appropriate strength of preparation, and is excellent in long-term storage stability.

What is claimed is:

1. A solid preparation comprising:
   (i) lansoprazole or voglibose,
   (ii) one or more water-soluble sugar alcohols selected from the group consisting of sorbitol, maltitol, reduced starch saccharide, xylitol, reduced palatinose and erythritol, and
   (iii) low-substituted hydroxypropylcellulose having hydroxypropoxyl group contents of 7.0 to 9.9 percent by weight; wherein said low-substituted hydroxypropylcellulose is incorporated in an amount of 3 to 50 weight parts per 100 weight parts of the solid preparation;
   wherein said solid preparation is capable of buccal disintegration or dissolution.

2. A solid preparation according to claim 1, wherein the water-soluble sugar alcohol is erythritol.

3. A solid preparation according to claim 1, wherein the water-soluble sugar alcohol is incorporated in an amount of 5 to 97 weight parts per 100 weight parts of the solid preparation.

4. A solid pharmaceutical preparation according to claim 1, which is a tablet.

5. A method for use of low-substituted hydroxypropylcellulose having hydroxypropoxyl group contents of 7.0 to 9.9 percent by weight for the manufacture of a pharmaceutical preparation capable of buccal disintegration or dissolution comprising blending a pharmaceutically active ingredient, one or more water-soluble sugar alcohols and a low-substituted hydroxypropylcellulose having hydroxypropoxyl group contents of 7.0 to 9.9 percent by weight to form a solid preparation;

molding said preparation; and optionally drying said preparation.

6. A method of improving buccal disintegration or dissolution of a solid pharmaceutical preparation comprising adding a low-substituted hydroxypropylcellulose having hydroxypropoxyl group contents of 7.0 to 9.9 percent by weight to a solid pharmaceutical preparation.

7. A method for preparing a solid preparation comprising blending a pharmaceutically active ingredient, one or more water-soluble sugar alcohols selected from the group consisting of sorbitol, maltitol, reduced starch saccharide, xylitol, reduced palatinose and erythritol and a low-substituted hydroxypropylcellulose having hydroxypropoxyl group contents of 7.0 to 9.9 percent by weight to form a solid preparation;

molding said preparation and then optionally drying said preparation;

wherein said solid preparation is bucally dissolved in from about 5 to about 50 seconds.

8. A method for improving buccal disintegration of a solid pharmaceutical preparation comprising blending a pharmaceutically active ingredient, one or more water-soluble sugar alcohols selected from the group consisting of sorbitol, maltitol, reduced starch saccharide, xylitol, reduced palatinose and erythritol with a low-substituted hydroxypropylcellulose having hydroxypropoxyl group contents of 7.0 to 9.9 percent by weight to form a solid preparation;

wherein said solid preparation is bucally dissolved in from about 5 to about 50 seconds.

9. The method of claim 7, wherein said solid preparation is bucally dissolved in from about 5 to about 40 seconds.

10. The method of claim 7, wherein said solid preparation is bucally dissolved in from about 5 to about 30 seconds.

11. The method of claim 8, wherein said solid preparation is bucally dissolved in from about 5 to about 40 seconds.

12. The method of claim 8, wherein said solid preparation is bucally dissolved in from about 5 to about 30 seconds.

13. A method for preparing a solid preparation comprising blending a pharmaceutically active ingredient, one or more water-soluble sugar alcohols selected from the group consisting of maltitol, reduced starch saccharide, xylitol, reduced palatinose and erythritol, and a low-substituted hydroxypropylcellulose having hydroxypropoxyl group contents of 7.0 to 9.9 percent by weight to form a solid preparation;

molding said preparation and then optionally drying said preparation;

wherein said solid preparation is bucally dissolved in from about 5 to about 50 seconds.

14. A method for improving buccal disintegration of a solid pharmaceutical preparation comprising blending a pharmaceutically active ingredient and one or more water-soluble sugar alcohols selected from the group consisting of maltitol, reduced starch saccharide, xylitol, reduced palatinose and erythritol, with a low-substituted hydroxypropylcellulose having hydroxypropoxyl group contents of 7.0 to 9.9 percent by weight to form a solid preparation;

wherein said solid preparation is bucally dissolved in from about 5 to about 50 seconds.

15. A solid preparation comprising:

(i) lansoprazole or voglibose, (ii) erythritol, and (iii) low-substituted hydroxypropylcellulose having hydroxypropoxyl group contents of 7.0 to 9.9 percent by weight, wherein said low-substituted hydroxypropylcellulose is incorporated in an amount of 3 to 50 weight parts per 100 weight parts of the solid preparation, wherein said preparation is capable of buccal disintegration or dissolution.

16. A method for preparing a solid preparation comprising blending a pharmaceutically active ingredient, erythritol and a low-substituted hydroxypropylcellulose having hydroxypropoxyl group contents of 7.0 to 9.9 percent by weight to form a solid preparation;

molding said preparation and then optionally drying said preparation;

wherein said solid preparation is bucally dissolved in from about 5 to about 50 seconds.

17. A method for improving buccal disintegration of a solid pharmaceutical preparation comprising blending a pharmaceutically active ingredient and erythritol with a low-substituted hydroxypropylcellulose having hydroxypropoxyl group contents of 7.0 to 9.9 percent by weight to form a solid preparation;

wherein said solid preparation is bucally dissolved in from about 5 to about 50 seconds.

18. A method for preparing a solid preparation comprising blending a pharmaceutically active ingredient, one or more water-soluble sugar alcohols selected from the group consisting of sorbitol, maltitol, reduced starch saccharide, xylitol, reduced palatinose and erythritol, and a low-substituted hydroxypropylcellulose having hydroxypropoxyl group contents of 7.0 to 9.9 percent by weight to form a solid preparation wherein said low-substituted hydroxypropylcellulose is incorporated in an amount of 5 to 40 weight parts per 100 weight parts of the solid preparation;

molding said preparation and then optionally drying said preparation;

wherein said solid preparation is bucally dissolved in from about 5 to about 50 seconds.

19. A method for improving buccal disintegration of a solid pharmaceutical preparation comprising blending a pharmaceutically active ingredient, one or more water-soluble sugar alcohols selected from the group consisting of sorbitol, maltitol, reduced starch saccharide, xylitol, reduced palatinose and erythritol, with a low-substituted hydroxypropylcellulose having hydroxypropoxyl group contents of 7.0 to 9.9 percent by weight to form a solid preparation wherein said low-substituted hydroxypropylcellulose is incorporated in an amount of 5 to 40 weight parts per 100 weight parts of the solid preparation;

wherein said solid preparation is bucally dissolved in from about 5 to about 50 seconds.

* * * * *